United States Patent [19]
Hollobaugh

[11] Patent Number: 5,209,219
[45] Date of Patent: May 11, 1993

[54] ENDOSCOPE ADAPTOR

[75] Inventor: Robert S. Hollobaugh, Columbus, Ohio

[73] Assignee: Laser Medical Research Foundation, Columbus, Ohio

[21] Appl. No.: 670,929

[22] Filed: Mar. 18, 1991

[51] Int. Cl.$^5$ .............................................. A61B 1/00
[52] U.S. Cl. ................................. 128/4; 128/6; 604/167; 604/247
[58] Field of Search ............... 128/4, 6; 604/167, 169, 604/246, 247, 264, 283, 905

[56] References Cited

U.S. PATENT DOCUMENTS

| | | | |
|---|---|---|---|
| 3,791,379 | 2/1974 | Storz | 128/4 |
| 3,805,770 | 4/1974 | Okada | 128/4 |
| 3,830,225 | 8/1974 | Shinnick | 128/4 |
| 4,211,214 | 7/1980 | Chikashige | 128/4 |
| 4,405,316 | 9/1983 | Mittleman | 604/247 |
| 4,502,502 | 3/1985 | Krug | 604/247 |
| 4,929,235 | 5/1990 | Merry et al. | 604/167 |
| 4,972,828 | 11/1990 | Ito | 128/4 |

Primary Examiner—Gene Mancene
Assistant Examiner—Frank A. LaViola
Attorney, Agent, or Firm—George Wolken, Jr.

[57] ABSTRACT

The present invention relates to an adapter apparatus for medical endoscopes. The present invention comprises an apparatus for inserting tightly into a typical access port of a medical endoscope. Such adapter apparatus permits certain medical implements, such as optical fibers for laser surgery, to be inserted therethrough for treatment of the patient. This adapter apparatus also permits simultaneous passage therethrough of saline or other irrigation fluid without the prior removal of the medical implement. This permits rapid, simultaneous irrigation to proceed directly through an existing endoscope channel.

3 Claims, 4 Drawing Sheets

ENDOSCOPE ADAPTOR

BACKGROUND OF INVENTION

This invention relates to the general field of medical devices, and more particularly to an apparatus for facilitating endoscopic medical and surgical procedures.

A basic tenent of modern surgery is to perform the necessary surgical procedure on the patient with minimum disturbance and destruction to intervening tissues and organs. Thus, endoscopes are finding a large role in surgery, giving the surgeon access to many parts of the body with minimum disturbance to intervening tissues by incision. For procedures performed in many body cavities (e.g. bronchus, lung, esophagus, etc.) access through an endoscope avoids completely the need for surgical incisions and the resulting trauma to the patient.

Specific endoscopes are available for access to particular body cavities. For example, bronchoscopes, sigmoidoscopes, gastroscopes, etc. are all available. The primary difference in these devices lies in the size. The general configuration and method of use are not essentially different from scope to scope. We will use the term "endoscope" herein as a generic term to indicate any such device.

A major disadvantage in performing surgery through an endoscope is the limited access the surgeon has to the surgical field. Thus, suction, irrigation, biopsy, incisions, and any other surgical procedures must compete for limited space in the typical endoscope channel. More and more surgery is being performed by means of laser light directed to the patient by an optical fiber passed through an endoscope. This adds to the demands for space in the endoscope channel, particularly as such modern procedures as photodynamic cancer treatments emerge from clinical tests into general use.

Endoscopes are made in a rigid configuration and also made flexible such that the surgeon can control the direction of the endoscope tip inside the patient's body, typically by means of a control wheel close to the eyepiece. The flexible endoscope is certainly more versatile in performing surgical procedures, but exacerbates the problems of access to the surgical field. That is, typical rigid endoscopes have more space for access by the surgeon. For this reason, the primary emphasis of the present invention is on flexible endoscopes. However, the use of the present device for rigid endoscopes is obvious in those cases in which it would be useful for the surgeon. Typically, however, the surgeon using a rigid endoscope would not have the severe limitations on access the present invention is intended to relieve.

The typical flexible endoscope has several devices and access ports mounted close to the eyepiece, easily accessible to the surgeon and assistant. In addition to the eyepiece for viewing the surgical field through optical fibers, there is typically a control wheel by means of which the surgeon can direct the tip of the endoscope to the desired location within the patient. There is also an illumination port through which light is delivered to the surgical field for viewing by the surgeon.

Such endoscopes typically have suction applied through the endoscope channel. Typically, suction is applied continuously to an inlet in the endoscope, near the eyepiece. The suction is not usually directed to the surgical field, having a nearby suction port connected to the suction inlet and open to the atmosphere. However, merely by covering this suction port, the surgeon can apply suction to the surgical field at will.

The more recent models of endoscopes have yet another access port through which the surgeon can access the tip of the endoscope. This is frequently called a "biopsy channel" since it can find use for removing a sample of tissue for analysis. When used for viewing and sampling a region of the patient, access through the biopsy channel by a biopsy device is typically adequate. However, as more and more surgery is performed through endoscopes, access by means of a single channel places a severe constraint on the surgeon. For example, in the performance of laser surgery or photodynamic therapy through the biopsy channel of the endoscope, there is no convenient way to irrigate the surgical field. For the laser surgeon to have irrigation of his working field, typically the surgical device must be removed, irrigation performed, and the device replaced and surgery continued. This obviously is tedious for the surgeon. More importantly, it prolongs the duration of surgery for the patient including the patient's time under anesthesia.

The present device is an adapter for endoscopes allowing the biopsy channel to perform irrigation as well as another (typically laser) procedure at the same time. Thus, by using the present device, the surgeon can keep the optical fiber in place in the biopsy channel for performing the procedure, quickly have irrigation of the field when needed, and promplty return to the procedure with minimal interruption for the irrigation. The result is a marked increase in convenience to the surgeon, and a more rapid (hence, safer) procedure for the patient.

SUMMARY AND OBJECTS OF INVENTION

The present invention relates to an adapter for a surgical endoscope allowing the surgeon simultaneously to irrigate and to perform the surgical procedure using the same endoscope channel.

A primary object of the present invention is to allow irrigation of surgical fields through an endoscope channel without removing the optical fiber or other device accessing said surgical field through the same endoscope channel.

Another object of the present invention is to provide an adapter for existing endoscope allowing simultaneous irrigation and surgery to occur using the same endoscope channel.

Yet another object of the present invention is to reduce the duration of surgical procedures using an endoscope by facilitating access to the surgical field.

DESCRIPTION OF PREFERRED EMBODIMENTS

Figure 1:
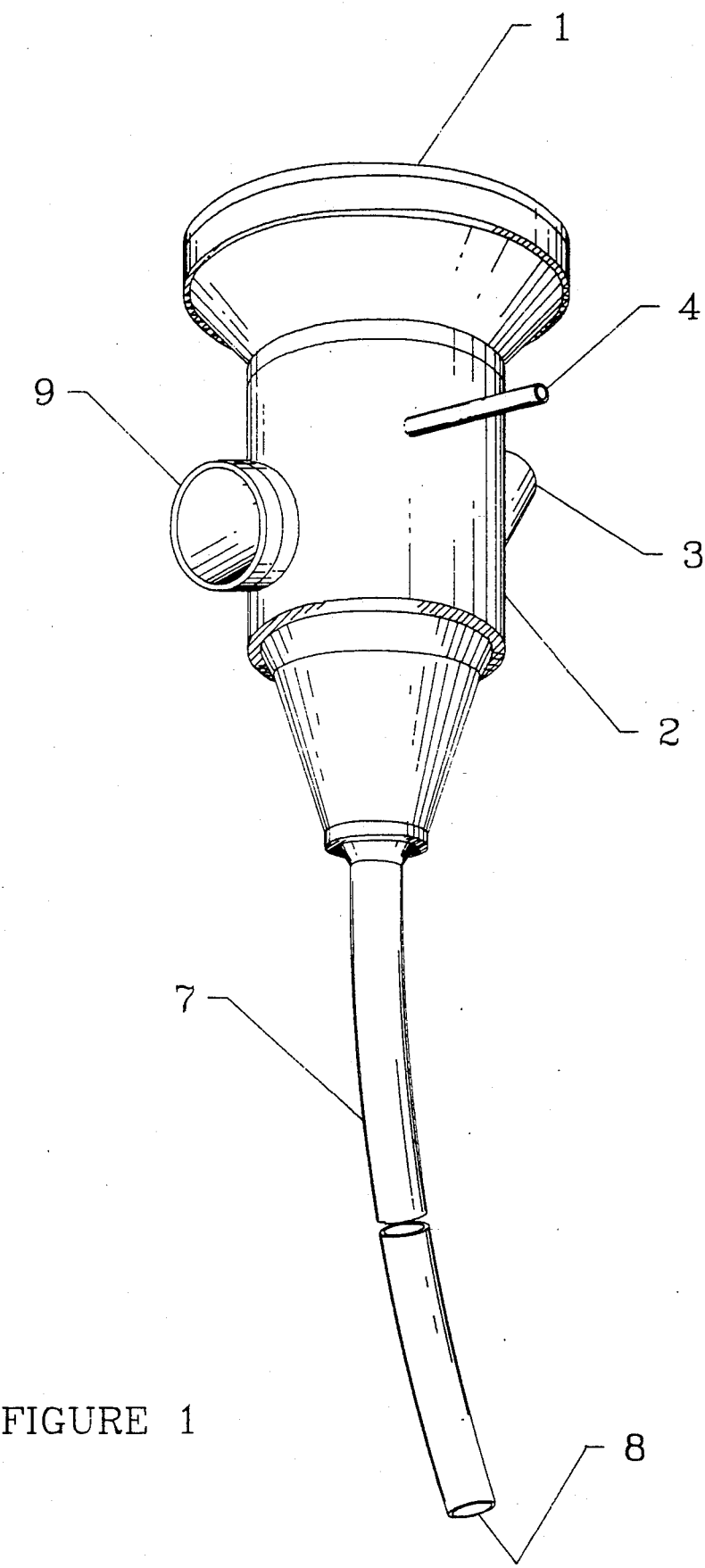
FIG. 1: Schematic side view of typical flexible endoscope with typical configuration of access ports.

FIG. 1 shows a typical flexible endoscope in schematic view. An eyepiece for viewing, 1, terminates the upper end of the endoscope, 2. This is attached to the cable, 7, which can have various lengths for various purposes. The opposite end, 8, of the endoscope cable is to be inserted into the patient for viewing, or for performing other surgical and medical procedures.

In these descriptions and drawings we illustrate the example of a flexible endoscope, believing such will be the typical preferred mode of usage for the present invention. However, it should be clear from the following description that no essential feature of the present invention depends upon the flexibility of the endoscope. Therefore, rigid endoscopes can very readily be used with the present adapter invention for those cases in which it provides an advantage for the surgeon.

The view of FIG. 1 also shows some of the typical controls and ports present on endoscopes. Typically, there will be a small control handle, 9, used to control the positioning of the endoscope tip, 8 within the patient. Some models of endoscopes have more than one control handle for control of more degrees of motion of tip, 8.

Typically, endoscopes have an illumination port, 3, whose function is to transmit light from an external source of illumination (not shown) to the surgical field, to provide adequate illumination for the surgeon. This light will typically be delivered to the surgical field and endoscope tip, 8 by means of an optical fiber or bundle of optical fibers.

Figure 2:
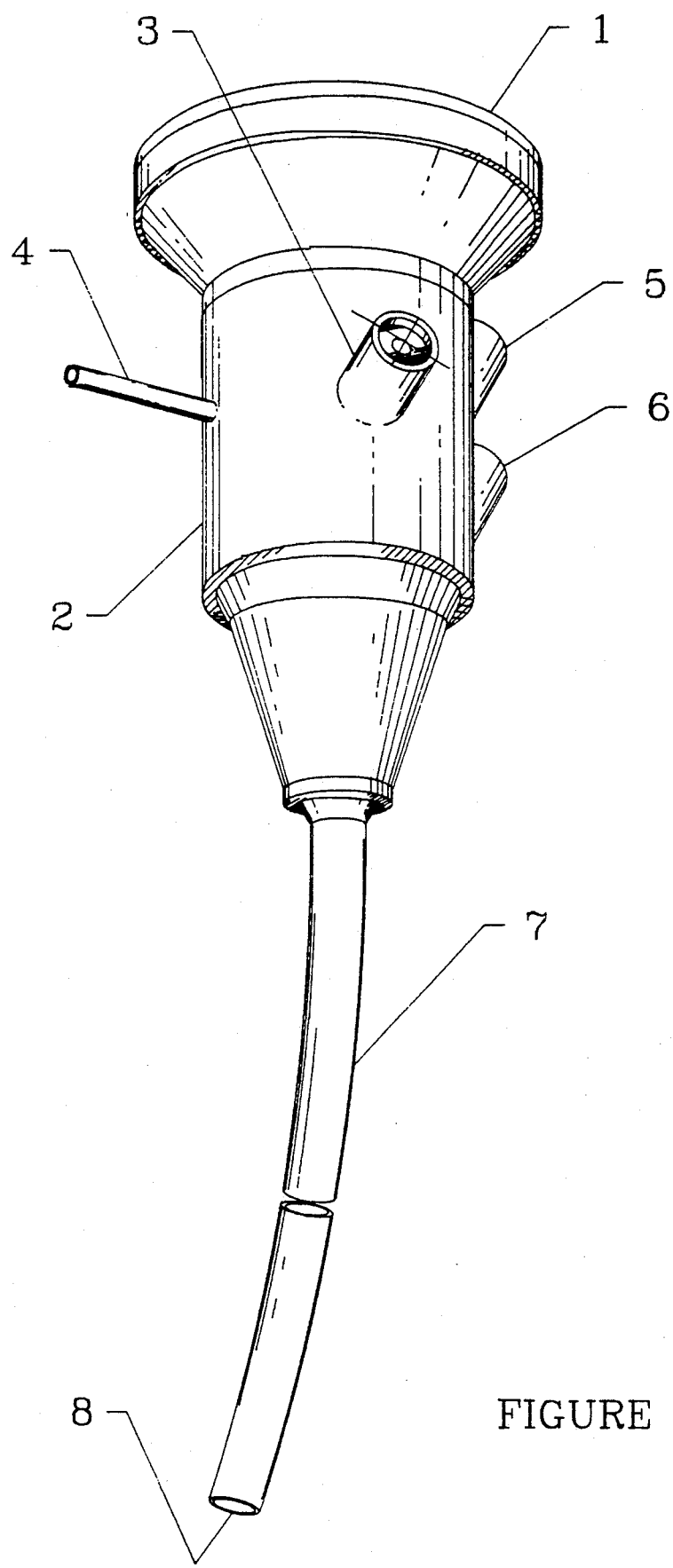
FIG. 2: Schematic front view of typical flexible endoscope with typical configuration of access ports (rotated 90° from FIG. 1).

Endoscopes also will typically have an inlet port, 4, for connection to an external source of suction. Shown as 5 in FIG. 2 is the "suction port". In normal operation the continuous suction applied to the endoscope through inlet port 4 will simply suck air through suction port 5 without delivering suction to the tip, 8, of the endoscope or to the surgical field. Merely by blocking port 5, the surgeon can cause suction to be delivered to the endoscope tip, 8 and surgical field for removal of various unwanted fluids and debris.

Many of the more recent endoscopes will also be provided with a "biopsy port", 6. The function of this port is to provide access to the endoscope tip, 8 and the surgical field. Typically, when the endoscope is used for viewing, the surgeon may find it convenient to remove a sample of tissue for analysis. Biopsy port, 6 allows this to be accomplished.

However, as more sophisticated surgical procedures are employed, port 6 may also be used for the performance of procedures other than biopsy. For example, in laser surgery, the laser light for performing the surgical procedure could be delivered to the surgical field by means of an optical fiber inserted into port 6 and terminating in the vicinity of the endoscope tip, 8. Likewise, for the photodynamic treatment of cancer, the treating light can be delivered through an optical fiber inserted into port 6.

However, when performing a surgical procedure through port 6, it is frequently convenient for irrigation to be performed simultaneously, or intermittently, during the procedure. Present devices do not permit simultaneous irrigation. With present devices it is required that a device be removed from the endoscope (typically, the device in port 6), irrigation be performed, and the device reinserted for continuation of the surgery. This is obviously tedious on the surgeon, fails to provide prompt irrigation to the patient as soon or as often as needed, and prolongs the time of the operation (and, often the time the patient spends under anaesthesia as well). It is a main object of the present invention to provide a simple apparatus for insertion into port 6 which permits irrigation of the surgical field whenever required while simultaneously leaving the device (typically an optical fiber) in place in port 6.

Figure 3:
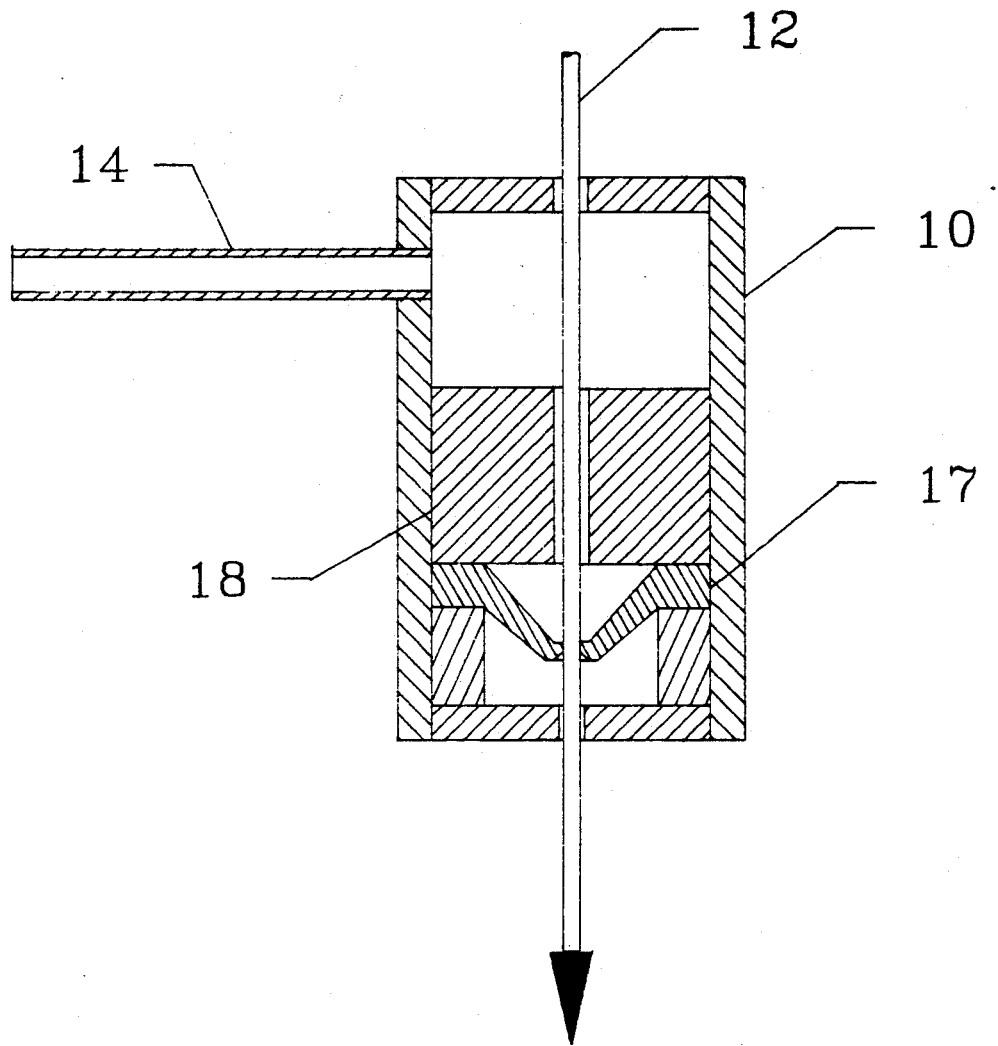
FIG. 3: Schematic cut-away view of adapter apparatus.

FIG. 3 shows a schematic cut-away view a typical adapter device according to the present invention. The device of FIG. 3 is cylindrical in shape, FIG. 3 showing merely a longitudinal cross sectional view. The main body of the present apparatus is a cylindrical, hollow object 10. Such main body, 10 can be chosen to have the size and flexibility to provide a tight seal with the port 6 in much the manner of a rubber stopper. However, it is convenient to perform this sealing function by means of a separate sealing plug, 16 in FIG. 4.

The present adapter device is provided inside body 10 with a back-up plug, 18. The function of this back-up plug is to provide a tight seal against the passage of substantial amounts of gas or fluid except as allowed through the one-way access device, 17. Typically, one-way access 17 will be a rubber protrusion with a small hole. The optical fiber (or other device), 12 is inserted through back-up plug, 18 and one-way access 17 and to the surgical field in the patient in the direction of the arrow. Back-up plug, 18 provides easy insertion and removal of fiber 12 without allowing the passage of substantial gas or fluids in the direction opposite the arrow.

Irrigation is provided by means of inlet 14. When irrigation is desired, saline (or any other irrigation fluid) is directed under pressure through the irrigation input port, 14. Such fluid is confined under pressure in the interior region of body 10, above the back-up plug, 18. When sufficient pressure is obtained, the irrigation fluid passes through one-way access, 17 to irrigate the surgical field. Removal of the irrigation fluid through suction inlet port 4 then follows.

Figure 4:
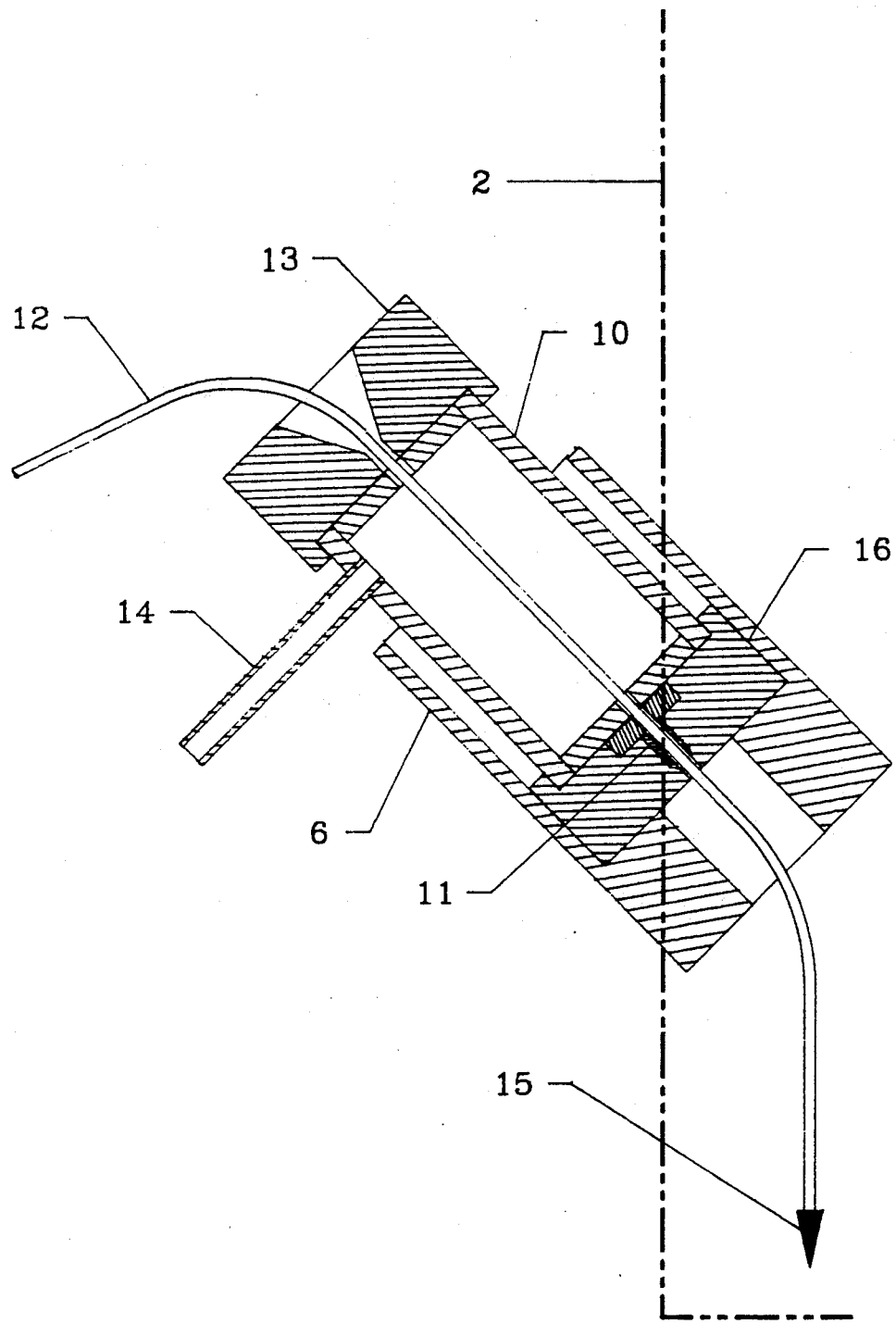
FIG. 4: Endoscope adapter of the present invention, as typically used in a flexible endoscope, shown in schematic, cut-away view and magnified.

The typical operation of the present adapter device is shown in FIG. 4. The main body, 10 is inserted into a sealing plug 16, typically with the assistance of a guiding plug, 11 to help ease alignment and fit. Such a plug, 16 needs the appropriate diameter and flexibility to fit snugly into port 6 in much the manner of a rubber stopper. Sealing plug, 16 must fit sufficiently tightly into port 6 that suction applied to the surgical field is removed via 14, and does not have an alternative path through port 6. Various sizes of plug 16 will be necessary for different sizes of endoscopes and different sizes of ports.

It is convenient to surmount the main body of the adapter apparatus, 10 with an access plug, 13 to ease the insertion of the fiber 12 through port 6 and into the patient along direction 15.

In operation, the surgeon requests irrigation at will. Typically the assistant will then inject saline (or another suitable solution) through port 14. The pressure of said irrigating solution will open one-way access 17, allowing the irrigating solution to flow to the surgical field through the endoscope channel in direction 15. Without interruption of the surgical procedure, irrigation is thereby accomplished quickly and easily.

I claim:

1. An adapter apparatus for a medical endoscope comprising;

a) a hollow, cylindrical main body having one opening in each longitudinally opposite end thereof, permitting passage of a thin, long medical implement therethrough;

b) interior to said main body, a plug dividing the interior region of said main body into an upper and lower region, said plug permitting the passage of said medical implement therethrough, and said plug having therein a one-way means for passage of fluid from the upper region of said main body to the lower region thereof, while preventing passage of fluid in the reverse direction; and, c) a means for introducing fluid into said upper region of said main body, said fluid having sufficient pressure to pass through said one-way means into the lower region of said body; and, d) a sealing plug attached longitudinally on the exterior of the lower region of said main body, said sealing plug having size and flexibility to cause a tight seal when inserted in an access port of said endoscope, and said sealing plug having a hole completely therethrough, said hole being in flexible material permitting the passage of said medical implement therethrough while providing a fluid-impermeable barrier therearound; and, e) a rigid guiding plug longitudinally connecting said main body with said sealing plug, said guiding plug facilitating the passage of said medical implement from said main body through said sealing plug.

2. An adapter apparatus for a medical endoscope as in claim 1, further comprising;

f) an access plug attached longitudinally on the exterior of the upper region of said main body, said access plug facilitating the insertion of said medical implement into said main body.

3. The combination of a medical endoscope and an adapter apparatus therefor comprising:

a) A medical endoscope having access ports on the external, viewing end thereof; and, b) a hollow, cylindrical main body having one opening in each longitudinally opposite end thereof, permitting passage of a thin, long medical implement therethrough;

c) interior to said main body, a plug dividing the interior region of said main body into an upper and lower region, said plug permitting the passage of said medical implement therethrough, and said plug having therein a one-way means for passage of fluid from the upper region of said main body to the lower region thereof, while preventing passage of fluid in the reverse direction; and, d) a means for introducing fluid into said upper region of said main body, said fluid having sufficient pressure to pass through said one-way means into the lower region of said body; and, e) a sealing plug attached longitudinally on the exterior of the lower region of said main body, said sealing plug having size and flexibility to cause a tight seal when inserted in an access port of said endoscope, and said sealing plug having a hole completely therethrough, said hole being in flexible material permitting the passage of said medical implement therethrough while providing a fluid-impermeable barrier therearound; and, f) a rigid guiding plug longitudinally connecting said main body with said sealing plug, said guiding plug facilitating the passage of said medical implement from said main body through said sealing plug.

* * * * *